(12) United States Patent
O'Hara et al.

(10) Patent No.: US 11,064,994 B2
(45) Date of Patent: Jul. 20, 2021

(54) LAPAROSCOPIC SUTURING DEVICES, NEEDLES, SUTURES, AND DRIVE SYSTEMS

(71) Applicant: ReViable Surgical, Inc., Lutz, FL (US)

(72) Inventors: Derek O'Hara, Lutz, FL (US); Jack Pullo, Coral Springs, FL (US); Peter James Meinz, Minneapolis, MN (US)

(73) Assignee: ReViable Surgical, Inc., Lutz, FL (US)

( * ) Notice: Subject to any disclaimer, the term of this patent is extended or adjusted under 35 U.S.C. 154(b) by 212 days.

(21) Appl. No.: 16/203,036

(22) Filed: Nov. 28, 2018

(65) Prior Publication Data

US 2019/0090867 A1 Mar. 28, 2019

Related U.S. Application Data

(63) Continuation of application No. 15/792,749, filed on Oct. 24, 2017, now Pat. No. 10,143,465.

(Continued)

(51) Int. Cl.
*A61B 17/04* (2006.01)
*A61B 17/062* (2006.01)
(Continued)

(52) U.S. Cl.
CPC ...... *A61B 17/0469* (2013.01); *A61B 17/0482* (2013.01); *A61B 17/0485* (2013.01);
(Continued)

(58) Field of Classification Search
CPC ............ A61B 17/0469; A61B 17/0482; A61B 17/0485; A61B 17/0487; A61B 17/0491; A61B 17/06114; A61B 17/062; A61B 17/0625; A61B 2017/0488; A61B 2017/049; A61B 2017/06009; A61B 2017/06142; A61B 2017/06152;
(Continued)

(56) References Cited

U.S. PATENT DOCUMENTS 3,049,018 A 8/1962 Lusskin et al.
3,570,497 A * 3/1971 Lemole ............ A61B 17/12009
606/151

(Continued)

OTHER PUBLICATIONS

Boston Scientific, "Capio™ SLIM Suture Capturing Device: Building on the history, reducing the profile," 2013, 4 pages.
(Continued)

*Primary Examiner* — Kathleen S Holwerda
(74) *Attorney, Agent, or Firm* — Fenwick & West LLP

(57) ABSTRACT

Devices are provided for a suturing device used during laparoscopic surgical procedures. A suturing needle includes a shaft forming a rod axis; a curved body having a piercing tip at a first end and a base at a second end; and an arm extending radially from the shaft to the base of the curved body such that the curved body is positioned in a plane orthogonal to the rod axis of the shaft and rotatable about the shaft in the plane orthogonal to the rod axis. The suturing device includes a housing, a suturing needle, one or more sutures, a suture magazine configured to hold the one or more sutures, and a drive system, whereby the drive system may actuate the suturing needle to rotate in the plane orthogonal to the drive system, allowing the suturing needle to drive in to and out of tissue to apply a suture.

11 Claims, 17 Drawing Sheets

Related U.S. Application Data

(60) Provisional application No. 62/411,830, filed on Oct. 24, 2016.

(51) Int. Cl.
*A61B 17/06* (2006.01)
*A61B 34/30* (2016.01)
*A61B 17/00* (2006.01)
*A61B 17/29* (2006.01)

(52) U.S. Cl.
CPC ...... *A61B 17/0487* (2013.01); *A61B 17/0491* (2013.01); *A61B 17/06004* (2013.01); *A61B 17/0625* (2013.01); *A61B 17/06066* (2013.01); *A61B 17/06114* (2013.01); *A61B 17/06166* (2013.01); *A61B 17/29* (2013.01); *A61B 34/30* (2016.02); *A61B 2017/00004* (2013.01); *A61B 2017/00296* (2013.01); *A61B 2017/00367* (2013.01); *A61B 2017/00477* (2013.01); *A61B 2017/00862* (2013.01); *A61B 2017/047* (2013.01); *A61B 2017/0496* (2013.01); *A61B 2017/0608* (2013.01); *A61B 2017/06009* (2013.01); *A61B 2017/06042* (2013.01); *A61B 2017/06076* (2013.01)

(58) Field of Classification Search
CPC .. A61B 2017/06157; A61B 2017/0496; A61B 2017/0608; A61B 17/064; A61B 17/12009; A61B 17/06166; A61B 2017/06176
See application file for complete search history.

(56) References Cited

U.S. PATENT DOCUMENTS

| | | | |
|---|---|---|---|
| 4,440,171 A | 4/1984 | Nomoto et al. | |
| 4,448,194 A * | 5/1984 | DiGiovanni | A61B 17/0491 112/80.05 |
| 4,484,580 A | 11/1984 | Nomoto et al. | |
| 5,215,090 A | 6/1993 | Hon et al. | |
| 5,437,681 A | 8/1995 | Meade et al. | |
| 5,484,095 A | 1/1996 | Green et al. | |
| 5,489,287 A * | 2/1996 | Green | A61B 17/04 227/176.1 |
| 5,707,379 A | 1/1998 | Fleenor et al. | |
| 6,120,526 A * | 9/2000 | Daley | A61B 17/064 606/176 |
| 7,338,502 B2 | 3/2008 | Rosenblatt | |
| 7,445,626 B2 | 11/2008 | Songer et al. | |
| 8,282,657 B2 | 10/2012 | McClurg et al. | |
| 10,143,465 B2 | 12/2018 | O'Hara et al. | |
| 2003/0018345 A1 | 1/2003 | Green | |
| 2009/0030434 A1 | 1/2009 | Paz et al. | |
| 2009/0093824 A1 | 4/2009 | Hasan et al. | |
| 2011/0152890 A1 | 6/2011 | Newell et al. | |
| 2012/0165838 A1 | 6/2012 | Kobylewski et al. | |
| 2014/0236193 A1 | 8/2014 | Chin et al. | |
| 2015/0351756 A1 | 12/2015 | Martin et al. | |
| 2018/0110511 A1 | 4/2018 | O'Hara et al. | |

OTHER PUBLICATIONS

Covidien, "Endo Stitch™: Suturing Instrument Intracorporeal Knot Tying Manual," 2008, 20 pages.

Onal, S., "Design of a New Suturing and Knot Tying Device for Laparoscopic Surgery," University of South Florida Scholar Commons, Graduate Theses and Dissertations, Aug. 31, 2010, 80 pages, Can be retrieved at URL: <http://scholarcommons.usf.edu/etd/3498>.

United States Office Action, U.S. Appl. No. 15/792,749, filed May 4, 2018, 10 pages.

United States Office Action, U.S. Appl. No. 15/792,749, filed Jan. 22, 2018, 14 pages.

PCT International Search Report and Written Opinion, PCT Application No. PCT/US2019/061257, dated Jan. 27, 2020, 14 pages.

* cited by examiner

LAPAROSCOPIC SUTURING DEVICES, NEEDLES, SUTURES, AND DRIVE SYSTEMS

CROSS REFERENCE TO RELATED APPLICATIONS

This application is a continuation of prior, co-pending U.S. application Ser. No. 15/792,749, filed on Oct. 24, 2017, which claims priority to U.S. Provisional Application No. 62/411,830, filed on Oct. 24, 2016, both of which are incorporated herein by reference in their entirety for all purposes.

BACKGROUND

Laparoscopic surgical procedures are becoming increasingly common as an alternative to open surgical procedures. Pain, hemorrhaging, and recovery time may be reduced when performing a laparoscopic surgical procedure versus an open surgical procedure. However, laparoscopic procedures can take longer to perform, which can increase the cost of performing the laparoscopic procedure and limit the amount of laparoscopic procedures that can be performed daily.

Suturing is a common method employed in surgeries to close tissue openings and secure synthetic objects to tissue, among other things. The suturing process is more challenging when being used in laparoscopic surgical procedures as there is a smaller space to work within and the degrees of movement that a surgeon is afforded is restricted as compared to open surgical procedures.

BRIEF SUMMARY

The following summary is provided to introduce a selection of concepts in a simplified form that are further described below in the detailed description. This summary is not intended to identify key features or essential features of the claimed subject matter, nor is it intended to be used to limit the scope of the claimed subject matter.

A suturing needle is provided that has a shaft forming a rod axis, a curved body having a piercing tip at one end and a base at another end; and an arm extending radially from the shaft to the base of the curved body such that the curved body is positioned in a plane orthogonal to the rod axis of the shaft and rotatable about the shaft in the plane orthogonal to the rod axis.

A suturing device incorporating the above described suturing needle can include one or more sutures, and a drive system. The drive system is coupled to the shaft and configured to actuate the rotation of the suturing needle in a first direction into tissue and a second direction that is opposite the first direction. The one or more sutures each include a fastener end, an anchor end, and a suture thread extending between the fastener end and the anchor end. A suture magazine can be used to hold the one or more sutures. The suturing needle and the suture magazine are positioned within a housing that allows for the suturing needle to exit the housing, catching the suture at the fastener end, as the suturing needle rotates in the first direction in the plane orthogonal to the rod axis.

A drive system for a suturing device can include a tube having a proximal end that may abut a hub that couples to a manual or robotic arm, a distal end that couples to a shaft of a suturing needle, and a rod having the hub at its distal end and one more protrusions on the rod in a position towards the proximal end of the rod and one or more grooves, each groove being for a corresponding one of the one protrusions, the one or more grooves extending in a spiral manner from a proximal end of the tube towards the distal end of the tube. The one or more protrusions on the rod are configured to move along the one or more grooves of the tube. The rod is configured to remain fixed along a direction of a tube axis of the shaft while being able to rotate about the tube axis. The tube is configured to remain fixed in a radial direction while being moveable forward and backward along the tube axis, the moving of the tube in the forward and backward direction causing the one or more protrusions of the rod to move along the one or more grooves and thereby rotate the rod and the shaft that would be coupled thereto about the tube axis. In another implementation, the protrusions may be in the tube and the grooves on the rod.

These and other features and advantages will be apparent from a reading of the following detail description, and a review of the appended drawings. It is to be understood that the foregoing summary, the following detail descriptions, and the appended drawings are only explanatory and are not restrictive of various aspects claimed.

BRIEF DESCRIPTION OF DRAWINGS

FIG. 3A shows a view of a suturing device over tissue in a middle position; FIG. 3B shows a view of a suturing device over tissue in an end position; FIG. 3C shows a cross-sectional view of a suturing device over tissue in an end position; FIG. 3D shows a view of a suture housing that is filled with sutures; FIG. 3E shows a view of an empty suture housing.

DETAILED DESCRIPTION

Figure 1A:
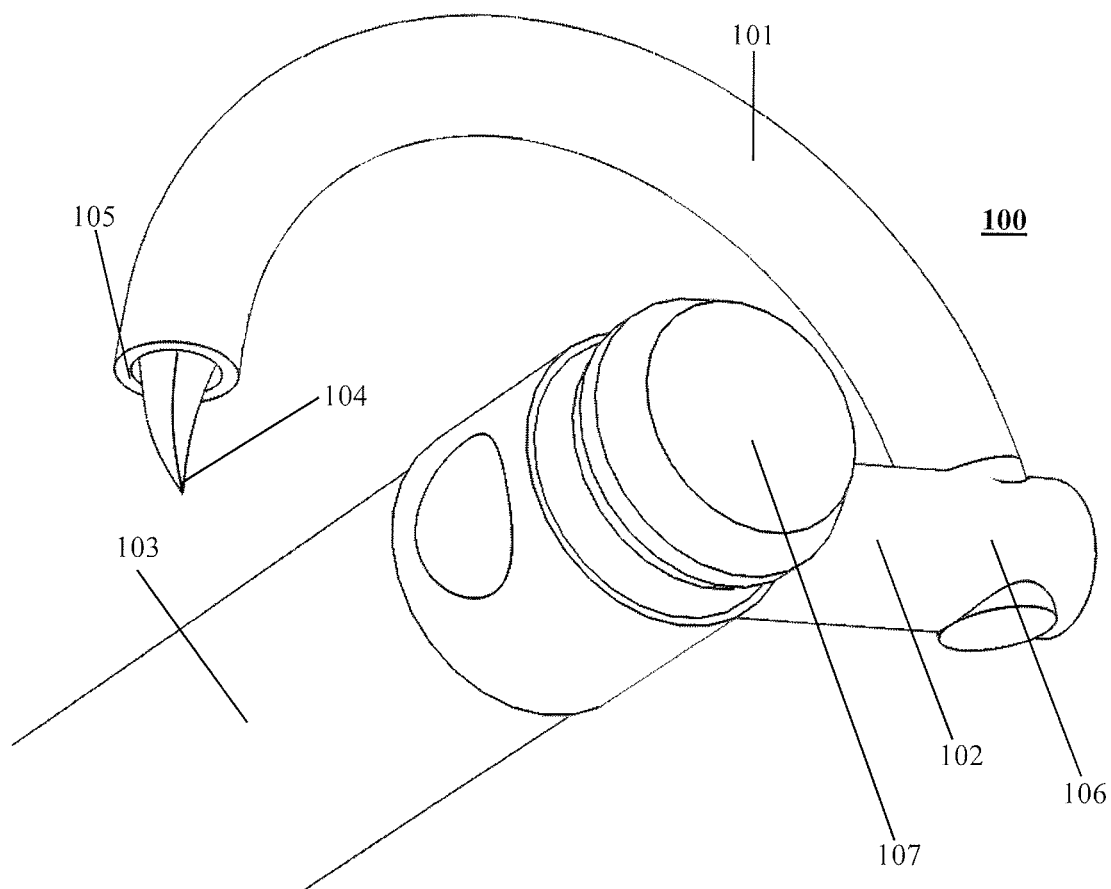
FIG. 1A shows a suturing needle in accordance with an implementation of the invention.

Implementations of the invention provide devices to improve suturing techniques in laparoscopic surgical procedures. Certain implementations of the invention enable surgeons to perform suturing procedures more efficiently even with the challenges presented by the restricted movement inherent in laparoscopic procedures.

Laparoscopic procedures can be performed manually or with a robotic-assisted surgical system. Manual laparoscopic surgical procedures involve cutting small incisions into the patient and placing tubes called ports through the incision site. The ports can include surgical instruments such as forceps, hooks, scissors, and more to mimic the movement and ability of the surgeon's hands. This allows the surgeon to perform the entire surgery ex vivo without physically placing their hands into the patient's body.

Alternatively, robotic-assisted laparoscopic procedures use a robotic-assisted surgical system that generally includes three or four robotic arms that the surgeon can manipulate from a distance at a console. Similar to the ports used in manual laparoscopic surgical procedures, at the console, the surgeon operates haptic controls that mimic the movement and ability of the surgeon's hands. With both manual laparoscopic procedures and robotic-assisted laparoscopic procedures, the surgeon must use instruments rather than their own hands to interact with tissue, making it difficult to reproduce functions that would normally be performed with a human hand. As a result, applying sutures to tissue during laparoscopic surgical procedures have become more cumbersome and tedious resulting in longer surgery times.

In particular, laparoscopic sacrocolpopexy, a surgical procedure used to treat vaginal vault or uterine prolapse, is susceptible to the challenges that current laparoscopic procedures present. A uterine prolapse results when the uterus descends from its normal position within the pelvis. Every year in the United States, approximately 300,000 women participate in pelvic organ prolapse corrective surgery. Sacrocolpopexy is a surgical technique that aims to reduce prolapse and restore the anatomy and function of the vagina by suturing a synthetic mesh to the vaginal wall. The mesh provides the vagina with support and requires about 12-15 sutures. Overall, the procedure can take three to four hours to complete, where the suturing process alone may require 60 to 100 minutes.

In order to address these challenges, certain implementations provide an efficient suturing device that, with a single motion, can stitch and tighten a suture, which diminishes the time, cost, and difficulty of laparoscopic surgeries.

Certain implementations involve automated stitching and tightening of sutures.

As used herein, the term "distal" end generally refers to the end that is further from the surgeon when the surgeon is operating the device.

Additionally, the term "proximal" end generally refers to the end that is closer to the surgeon when the surgeon is operating the device.

Figure 1B:
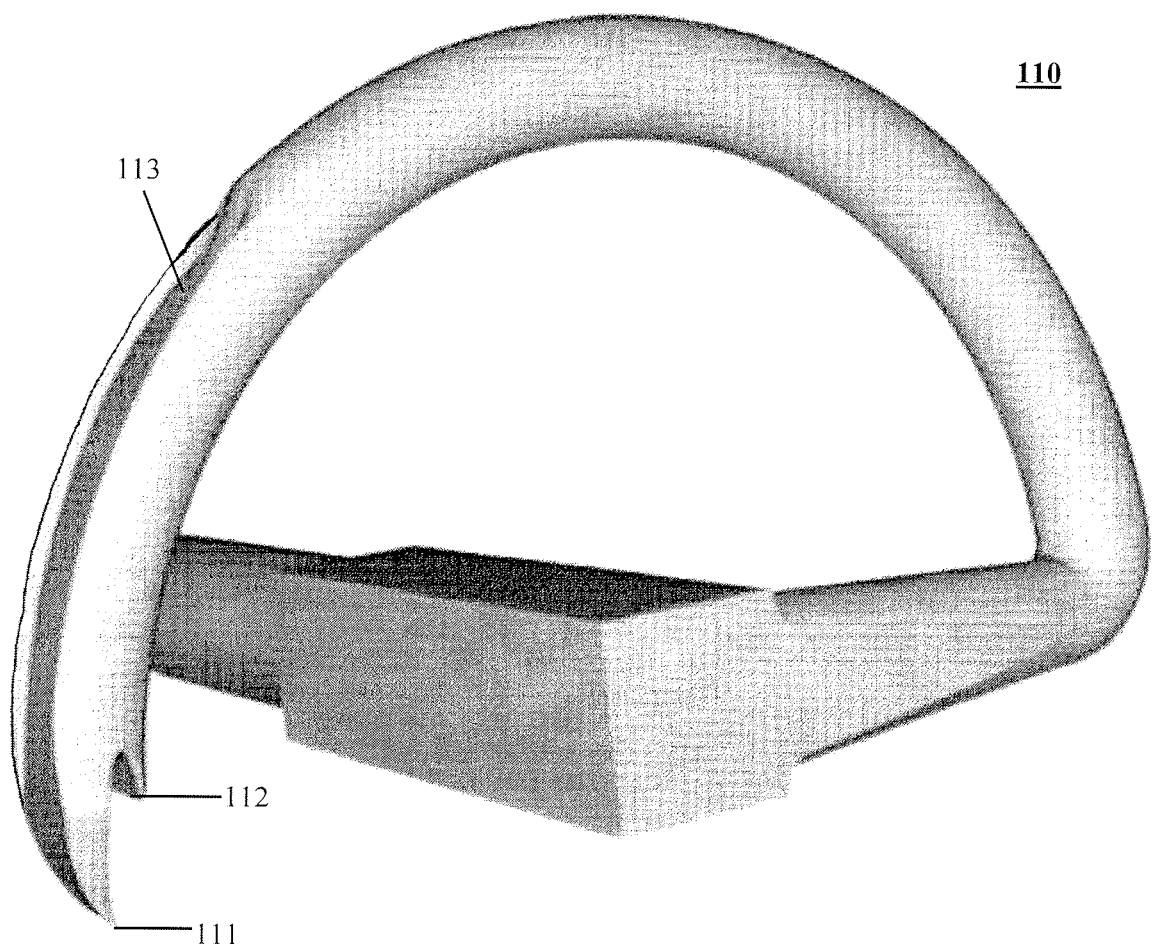
FIG. 1B shows an alternative suturing needle in accordance with an implementation of the invention.
Figure 1C:
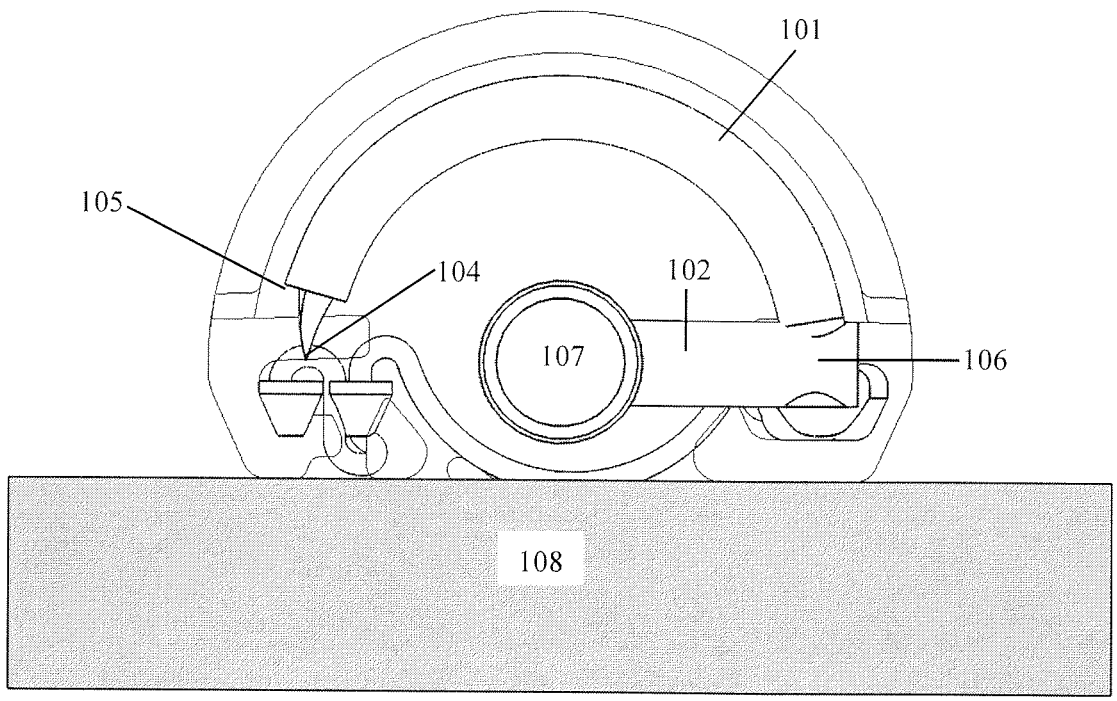
FIG. 1C shows a cross sectional view of a suturing device in a start position in accordance with an implementation of the invention.

FIGS. 1A, 1B, and 1C show a suturing needle 100 that can be used in a suturing device (explained in further detail below with respect to FIGS. 3A-3E). The suturing needle 100 has a curved body 101, an arm 102, and a shaft 103. The curved body 101 may have a piercing tip 104 at one end and a base 106 at the other end. The shaft 103 can form a rod axis 107. In one implementation, the suturing needle 100 may have a needle grasping edge 105 that is formed by the tube of the curved body 101 having a larger diameter than the base of the piercing tip 104. This allows the suture to be held along the needle grasping edge 105 as the curved body 101 rotates about the shaft 103. In an alternate implementation, the suturing needle 100 may also have a grasping element 112 that is configured to form a recess between the grasping element 112 and the piercing tip 111 so that a suture may be held in the recess as the curved body 101 rotates about the shaft 103. In another implementation, the needle may include a groove 113 extending from the piercing tip 104 along at least a portion of an outer surface of the curved body 101. The groove 113 can be configured to maintain a fastener portion of a suture in a position along the outer surface of the curved body 101 of the suturing needle 100.

The arm 102 extends radially from the shaft 103. The curved body 101 is positioned in a plane orthogonal to the rod axis 107 of the shaft 103 and rotatable about the shaft 103 in the plane orthogonal to the rod axis 107 to drive in to and out of a tissue 108 to apply a suture 200 (described in more detail below).

Figure 2A:
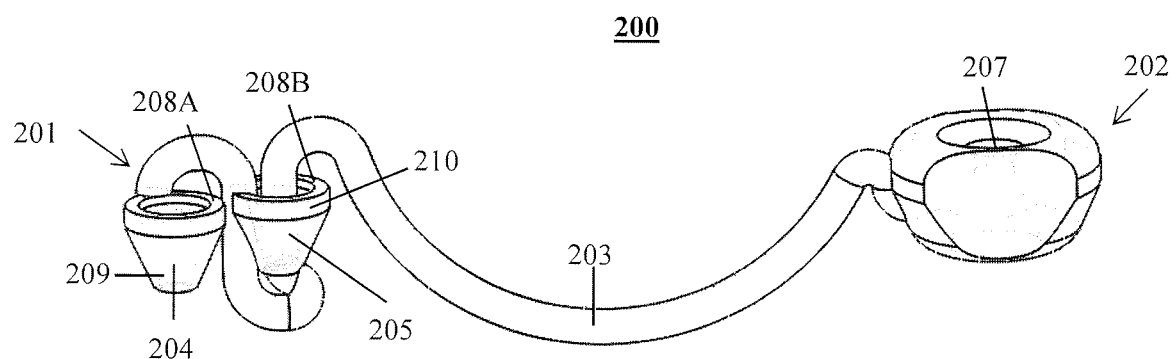
FIG. 2A shows a suture in accordance with an implementation of the invention.
Figure 2B:
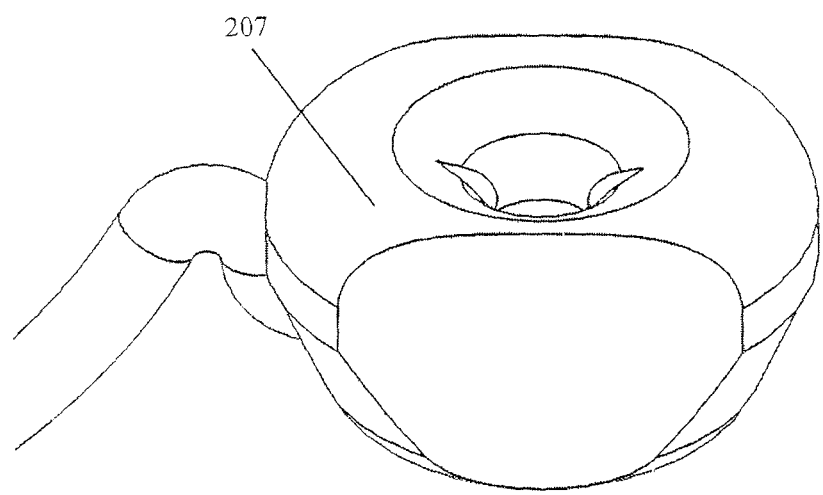
FIGS. 2B-2C show side views of a fastener end according to an implementation of the invention.

FIG. 2A illustrates an implementation of a suture 200 that may be used with a suturing device. A suture 200 can include a fastener end 201, an anchor end 202, and a suture thread 203 connected to and extending between the fastener end 201 and the anchor end 202. The fastener end 201 and the anchor end 202 may be made of polydllactide (PDLLA) or another biodegradable material. The suture thread 203 may be made of biodegradable material such as polydioxanone (PDS), polypropylene, or the like.

The suture 200 can include a first fastener mechanism 204 and a second fastener mechanism 205. Referring to FIG. 1 and FIGS. 2A-2C, as the suturing needle 100 rotates about the shaft 103, the piercing tip 104 is inserted through the first fastener mechanism 204. As the suturing needle 100 continues rotation, the needle grasping edge 105 secures the first fastener mechanism 204 and pulls it through the tissue 108 and through the chamber 206 of the anchor end 202 of the suture 200. The first fastener mechanism 204 can then be used to pull the second fastener mechanism 205 through the chamber 206 to tighten the suture 200 to pull the tissue 108 together.

In this implementation, as the first fastener mechanism 204 is moved through the chamber 206 (see FIG. 2C) of anchor housing 207 of the anchor end 202, the geometrical configuration locks the fastener grasping edge 208A of the first fastener mechanism 204 on top of the chamber 206 such that the first fastener mechanism 204 cannot be moved backwards through the chamber 206.

Referring to FIG. 2A, the fastener end 201 has a top 209 and a bottom 210. The suture thread 203 may be embedded in, molded in, or otherwise fixed to the top 209 of the fastener end 201. The bottom of the fastener end 201 may include a suture guide loop that performs part of the function of the first fastener mechanism, meaning that the suture guide loop can be secured by the grasping element 112 or other functionally similar structure and moved through the tissue 108 and into or through the anchor end 202 of the suture 200.

Figure 2C:
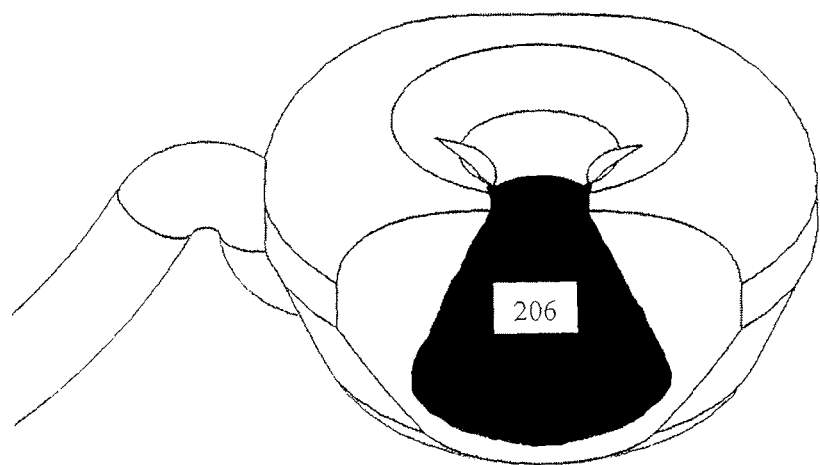

Referring now to FIG. 2C, the chamber 206 is contained within the anchor housing 207. The chamber 206 may have a conical shape. However, the shape of the chamber 206 and even the anchor end 202 can vary. For example, the chamber may be rectangular, curved, semi-spherical, or any other known shape that can function to receive the fastener end 201 of the suture 200 and secure the fastener end 201 to the anchor end 202. In an alternate embodiment, the suture thread 203 may be looped through the chamber 206 and tied around the anchor housing 207, and extend and connect to the fastener end 201. In another implementation, the suture thread 203 may be embedded in, molded in, or otherwise fixed to the anchor housing 207 of the anchor end 202.

When the first fastener mechanism 204 of the fastener end 201 passes through the chamber 206 in an upward direction, the conical shape of the chamber 206 receives the first fastener mechanism 204 and locks the first fastener mechanism 204 over the top of the chamber 206. This inhibits the fastener end 201 from returning backwards through the chamber 206.

It should be understood that the fastener end 201 and the anchor end 202 may utilize any known geometrical configurations and/or locking mechanisms and are not limited to any one particular configuration. For example, the fastener end may have one or more ridges, the ridges being similar to a barb on a fish hook. These ridges may be designed to lock into a chamber of the anchor end. The chamber can have a structure to facilitate the locking of the fastener end into the anchor end, such as a curved shoulder to allow for the ridges to enter the chamber, but not allowing the ridges to exit the chamber in the direction that the ridges entered into the chamber. Of course, the shape of the fastener end can vary and is not limited to having a surface with one or more ridges. For example, in another alternate implementation of the fastener end, the fastener end may have a flat surface and a surface with one or more ridges opposite from the flat surface.

The chamber may have one or more shoulders configured to allow the fastener end to enter the chamber in a unidirectional manner.

When the fastener end passes through the chamber in an upward direction, the ridges of the fastener end pass the shoulders. The ridges lay on top of the shoulders to inhibit the fastener end from moving in a downward direction. This inhibits the fastener end from escaping the chamber and secures the fastener end inside the anchor end. As stated above, the shape of the fastener end and the anchor end are not limited to the implementations previously stated, and various other shapes and configurations may be used to secure the fastener end to the anchor end.

Figure 3A:
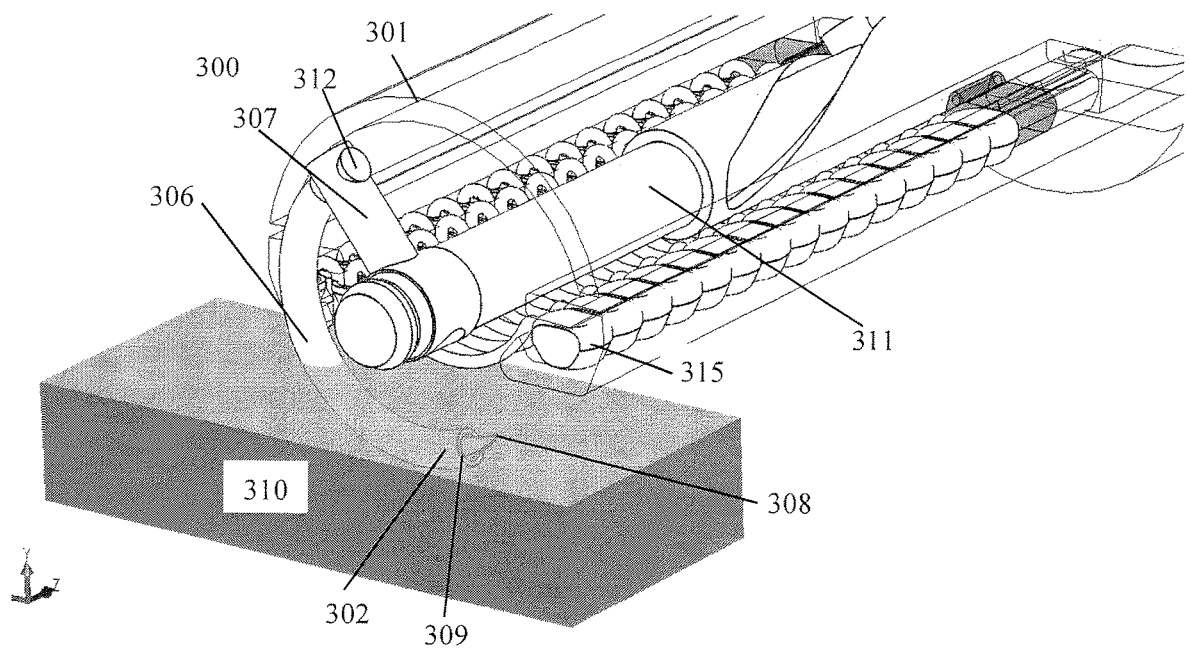
FIGS. 3A-3E show views of a suturing device and housing in accordance with an implementation of the invention.
Figure 3B:
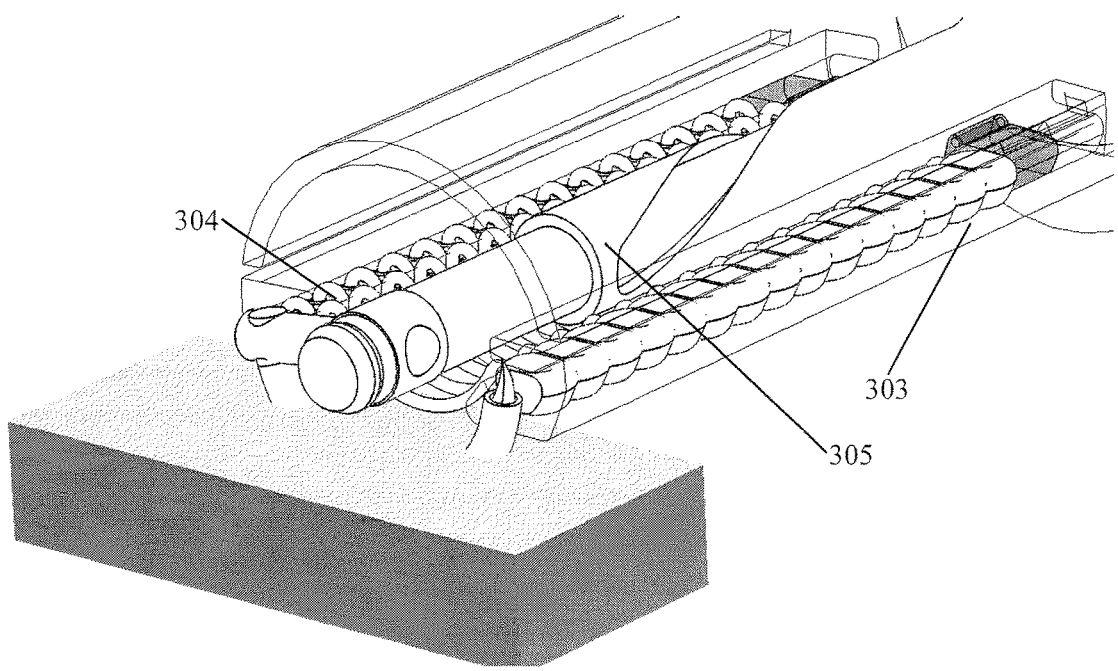
Figure 3C:
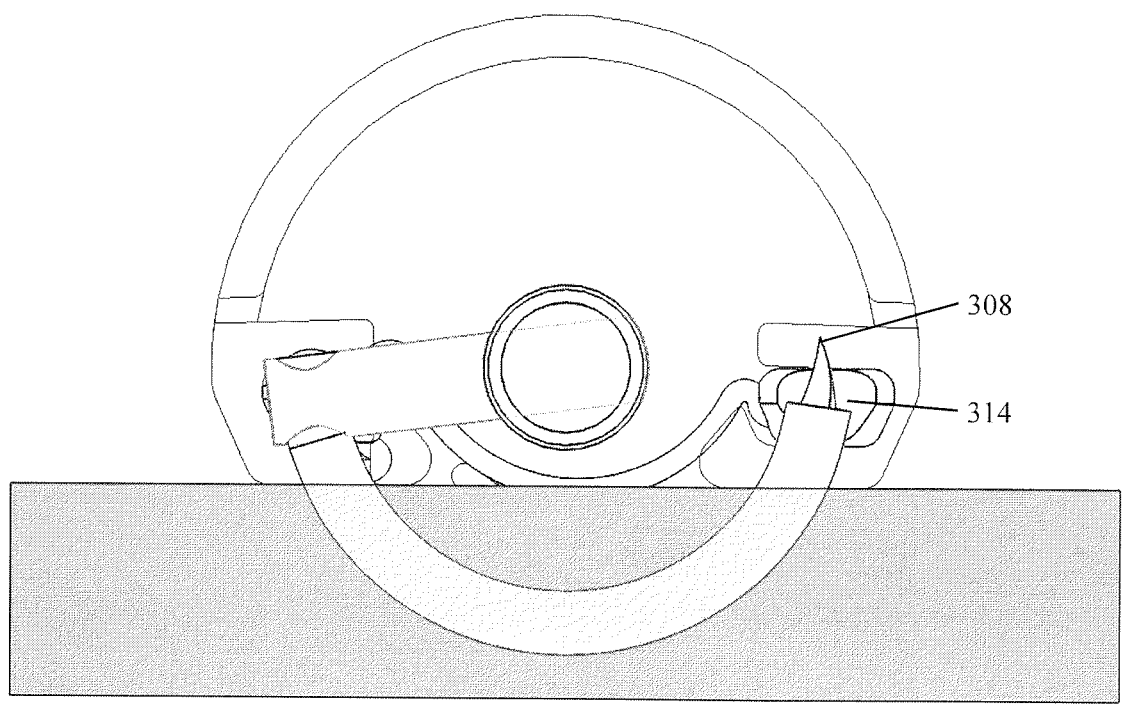
Figure 3D:
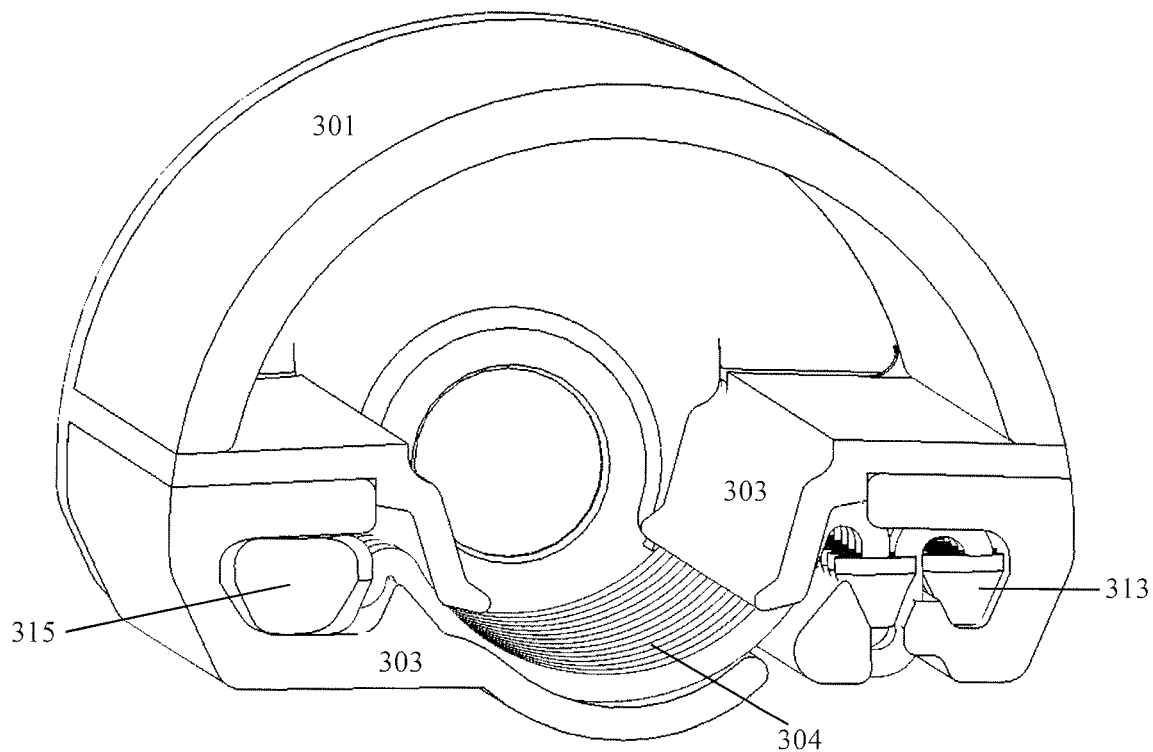
Figure 3E:
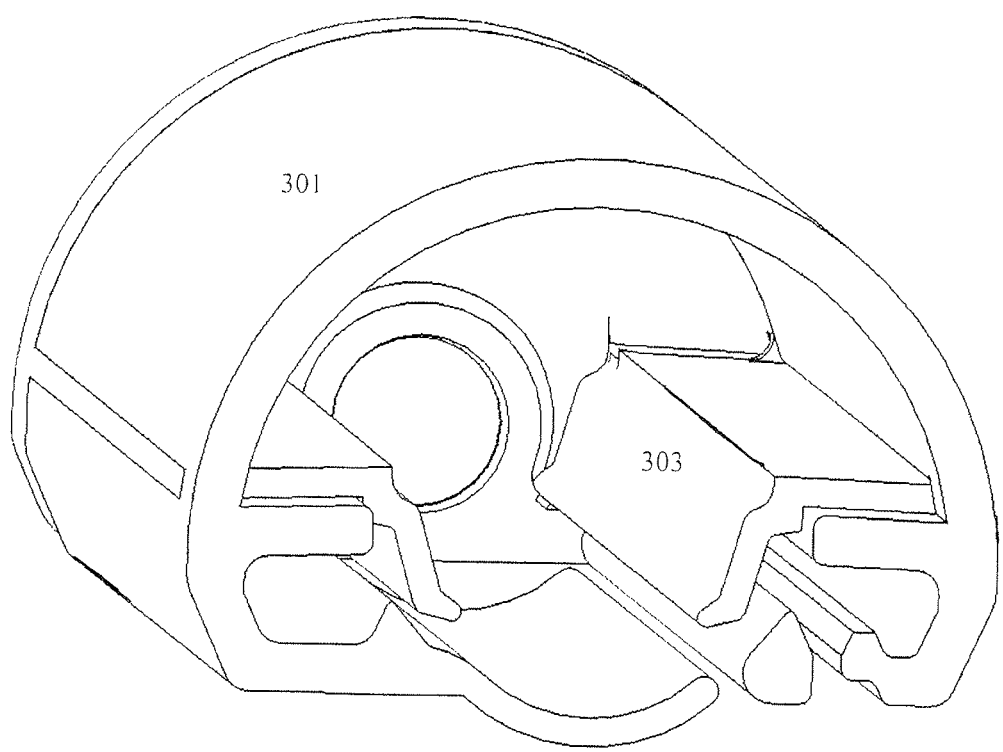

FIGS. 3A-3E show views of a suturing device and housing in accordance with an implementation of the invention. FIG. 3A shows a view of a suturing device over tissue in a middle position; FIG. 3B shows a view of a suturing device over tissue in an end position; FIG. 3C shows a cross-sectional view of a suturing device over tissue in an end position; FIG. 3D shows a view of a suture housing that is filled with sutures; FIG. 3E shows a view of an empty suture housing. As illustrated in FIGS. 3A-3E, a suturing device 300, in accordance with various implementations of the invention includes a suture housing 301, a suturing needle 302, one or more sutures 304, a suture magazine 303 configured to hold the one or more sutures 304, and a drive system 305 configured to actuate the rotation of the suturing needle 302 in a first direction into a tissue 310 and a second direction that is opposite the first direction to apply one or more sutures 304 to the tissue 310, or to apply one or more sutures 304 to mount an implant (e.g., synthetic mesh) onto the tissue 310.

Figure 4:
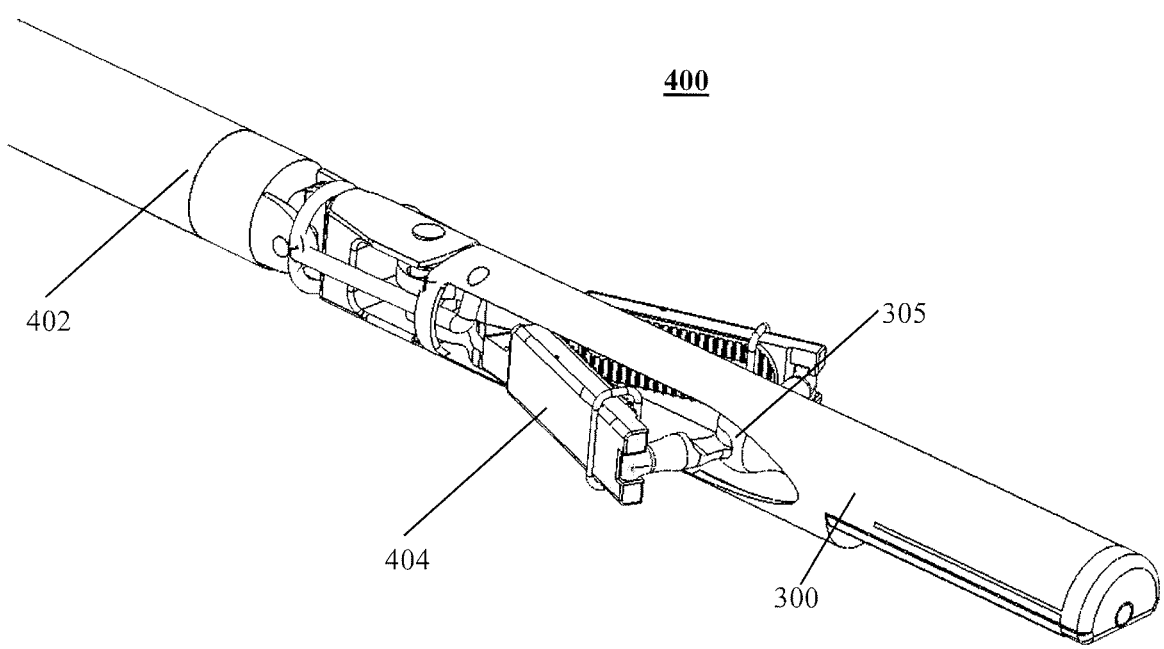
FIG. 4 shows a suturing device including a trigger according to an implementation of the invention.

FIG. 4 illustrates a laparoscope with suturing device. A laparoscope with suturing device 400 can be implemented, for example, with suturing device 300 mounted at a distal end of a standard laparoscope. The laparoscope may include a stem 402 and a trigger (not shown). The stem 402 of the laparoscope has a length long enough to allow the surgeon to operate the suturing device (e.g., device 300) from a location outside of the patient while the suturing device is in contact with tissue. The stem 402 is coupled to a drive system, for example, drive system 305, of the suturing device via clamps 404. The trigger (not shown) is located at the proximal end of the laparoscope. The surgeon can squeeze the trigger (not shown) to apply a force to the drive system 305 (via clamps 404), and thus engage the suturing device 300 to apply a suture.

In another implementation, the suturing device 300 may be mounted to the distal end of a robotic-assisted surgical forceps arm. A sheath made of a non-ridged sterile material may be used to connect the proximal end of the suture housing 301 to the distal end of the robotic-assisted surgical forceps arm. The sheath allows flexibility in orienting the suturing device 300 in different directions. The surgeon can close the forceps on the robotic-assisted surgical forceps arm to apply a force to the drive system 305, and thus engage the suturing device 300 to apply a suture 304. Alternatively, the suturing device 300 may be actuated as a robotic arm that works in tandem with a robotic-assisted surgical system. The surgeon can operate the suturing device 300 at a console to administer sutures 304.

Referring back to FIGS. 3A and 3B, the suture housing 301 of the suturing device 300 encloses the suturing needle 302, the one or more sutures 304, the suture magazine 303 configured to hold the one or more sutures 304, and the drive system 305. The suturing needle 302 can have a shaft 311 forming a rod axis 107, a curved body 306 having a piercing tip 308 at one end and a base 312 at another end, and an arm 307 extending radially from the shaft 311 to the base 312 of the curved body 306 so that the curved body 306 is positioned in a plane orthogonal to the rod axis 107 of the shaft 311 and rotatable about the shaft 311 in the plane orthogonal to the rod axis 107. The suturing needle 302 may also be designed in accordance with the suturing needle 100 or 110 as described in FIGS. 1A, 1B, and 1C.

The one or more sutures 304 of the suturing device 300 each comprises a fastener end, an anchor end, and a suture thread extending between the fastener end and the anchor end. The one or more suture may be designed in accordance with the suture illustrated in FIG. 2A. Additionally, the fastener end and the anchor end may be designed as described with respect to the fastener end illustrated in FIG. 2A, and the anchor end illustrated in FIGS. 2A, 2B, and 2C.

Figure 5A:
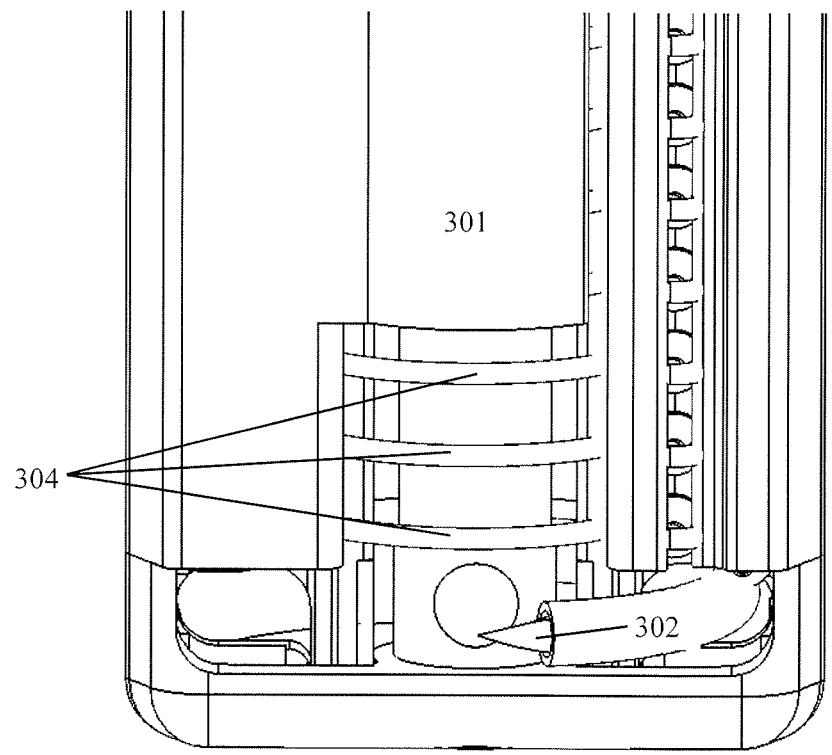
FIGS. 5A-5B show bottom views of a suturing device with sutures in accordance with an implementation of the invention.
Figure 5B:
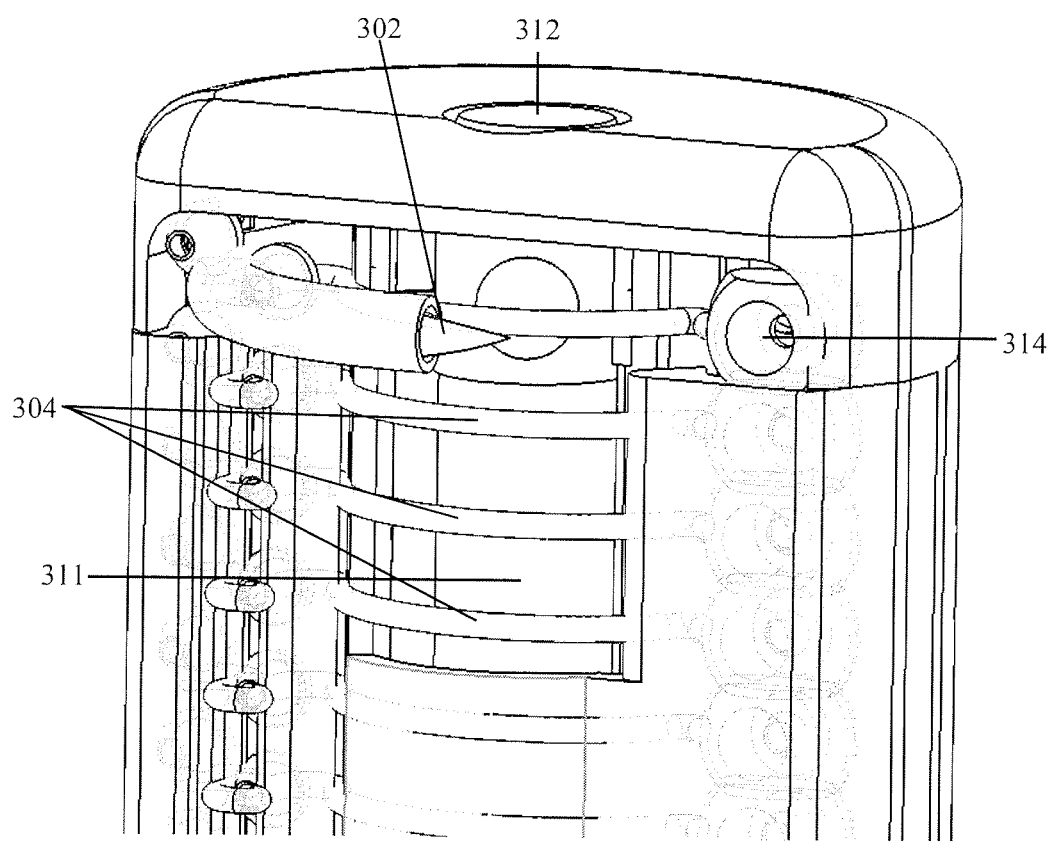

Referring now to FIGS. 5A and 5B, the suture housing 301 of the suturing device 300 has an aperture in the plane orthogonal to the rod axis of the suturing needle 302 that permits exiting of the suturing needle 302 and one of the one or more sutures 304 from the suture housing 301. The suture housing 301 may have a curved upper interior surface and a flat lower interior surface, where the aperture is in the flat lower interior surface. The curved upper interior surface of the suture housing 301 is slightly longer than the flat interior lower surface to allow the suturing needle 302 to rotate in to and out of the tissue 310 to apply a suture 304 (see FIGS. 3A, 3B, and 3C). However, the shape of the suture housing 301 can vary and is not limited to having a curved upper interior surface and a flat lower interior surface. In one implementation, the curved upper interior surface of the suture housing 301 may have a needle track that maintains the suturing needle 302 within the plane orthogonal to the rod axis of the suturing needle 302.

The suture housing 301 may be made of a rigid sterile material, and the suture housing 301 may be discarded after use, or sterilized and re-used for numerous procedures. Additionally, in one implementation, the suture magazine 303 may be discarded after use, and may be replaced with another suture magazine 303. The suture magazine 303 is configured to hold the one or more sutures 304 within the suture housing 301 so that the fastener end 201 of the one or more sutures 304 can be positioned to be grasped by one end of the curved body 101 of the suturing needle 302 as it exits the aperture in the suture housing 301 at one side of the shaft 103 of the suturing need 302, and the anchor end 202 can be positioned to exit the aperture in the suture housing 301 at another side of the shaft 103 of the suturing needle 302. The suture magazine 303 is seated on to the flat lower surface of the suture housing 301 towards the distal end of the suturing device 300.

Figure 6A:
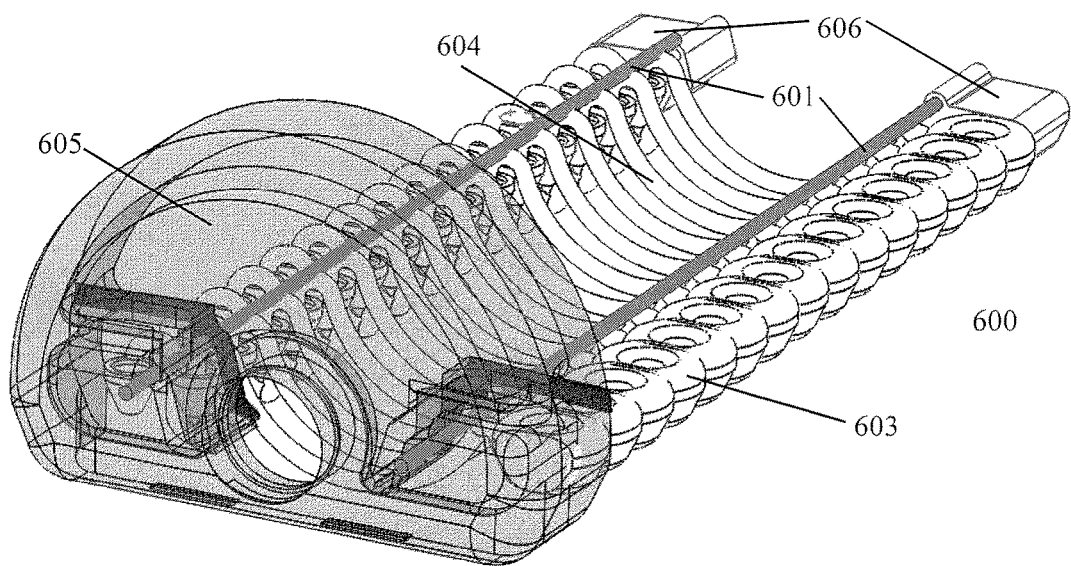
FIG. 6A shows a suture magazine and its various components, including a needle housing, in accordance with an implementation of the invention.

FIG. 6A illustrates an implementation of a suture magazine 600 that may be used in the suturing device 300 as shown in FIG. 3A. Each suture can have a fastener end 602, an anchor end 603, and a suture thread 604 connected to and extending between the fastener end 602 and the anchor end 603. The suture thread 604 may be made of biodegradable material such as polydioxanone (PDS), polypropylene, or the like. In one implementation, the suture may be designed in accordance with the suture illustrated in FIG. 2A. Additionally, the fastener end 602 and the anchor end 603 may be designed in accordance with the fastener end 201 illustrated in FIG. 2A and the anchor end 202 illustrated in FIGS. 2B and 2C. The suture magazine 600 can include elastic members 601. The elastic members 601 can be made of rubber or another elastic material. The elastic members 601 have a distal end that is towards the suture needle 100 and a proximal end that is towards the hub. The distal end of the elastic members 601 is attached to the suture housing cover 605 and the proximal end is attached to the suture movers 606. The suture movers 606 are configured to slide within the suture magazine 600 such that when a suture is used and leaves through the aperture in the suture housing 301, the force created by the elastic members 601 pulls the suture movers 606 forward which in turn pushes any remaining sutures forward towards the distal end of the suturing device 300. In an alternate embodiment, a spring can be placed on the proximal end (behind) of the suture movers 606 so that the sutures can be moved forward when a suture is used and leaves through the aperture in the suture housing 301. The spring can be used as a replacement to or in combination with the elastic members 601 to move the sutures forward each time a suture is used and leaves through the aperture in the suture housing 301. The spring/suture movers combination or the elastic members/suture movers combination may be used as a loading mechanism in contact with the suture magazine 600. The loading mechanism is not limited to these combinations. The loading mechanism may be any structure that can be tensioned to apply a force to the suture magazine 600.

Figure 6B:
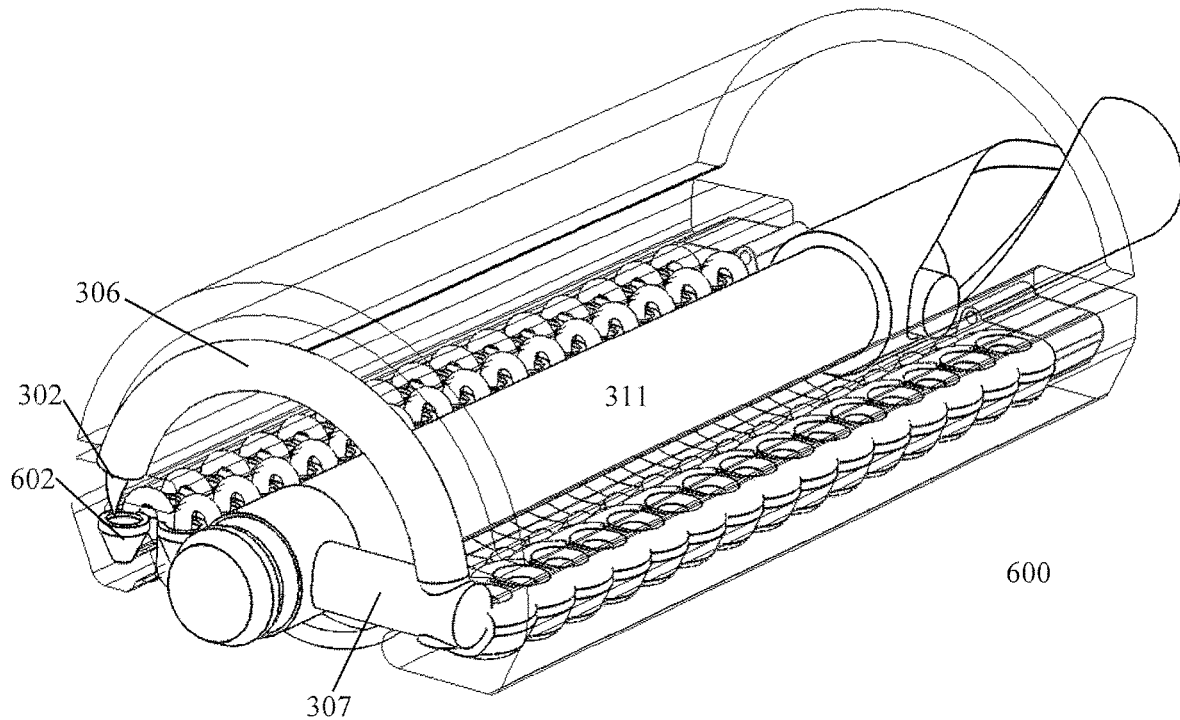
FIG. 6B shows a suture magazine positioned inside the housing of a suturing device according to an implementation of the invention.

FIG. 6B shows the suture magazine 600 positioned inside the suture housing 301 of the suturing device 300. When the suture magazine 600 is seated on to the flat lower interior surface of the suture housing 301, the suture thread 604 lays laterally behind the suturing needle 302 and across the flat lower interior surface of the suture housing 301. The suturing needle 302 can be actuated to rotate in the plane orthogonal to the tissue to drive in to and out of the tissue to apply a suture.

The suturing needle 302 has a curved body 306, an arm 307, and a shaft 311. The curved body 306 may have a piercing tip 308 at one end and a base 312 at the other end. The shaft 311 can form a rod axis. In one implementation, the suturing needle 302 may also have a grasping edge 309 that is configured to form an edge between the grasping edge 309 and the piercing tip 308. This allows for the piercing tip 308 to enter the tissue in a curved motion with the first fastener mechanism 313 in tow, and exit the tissue while simultaneously inserting the first fastener mechanism 313 through the chamber 314 or the anchor housing 315.

In an alternate embodiment, the needle may also include a groove 113 extending from the piercing tip 111 along at least a portion of an outer surface of the curved body 306. The groove 113 can be configured to maintain the fastener end 602 in a position along the outer surface of the curved body 306 of the suturing needle 302. In another implementation, the fastener end 602 can include a suture guide loop, and the grasping element 312 of the suturing needle 302 may grab the suture guide loop to pull the fastener end 602 from the belt and enter the tissue in a curved motion with the fastener end 602 in tow, and exit tissue while simultaneously inserting the fastener end 602 into the anchor end 603.

In one implementation, the suturing needle 302 can be actuated by the drive system 305. The drive system 305 is coupled to the shaft 311 of the suturing needle 302, whereby the curved body 306 is positioned in a plane orthogonal to drive system 305. The suturing needle 302 can rotate in a first direction and a second direction that is opposite the first direction, in the plane orthogonal to tissue from a starting position to an end position. In the starting position (see FIG. 1B), the curved body 306 of the suturing needle 302 is stationary inside the suture housing 301 in the plane orthogonal to the drive system 305, the fastener end 602 of the suture is in place for grasping by the suturing needle 302, and the anchor end 603 of that suture is positioned away from the aperture in the suture housing 301. In a motion to the end position, the needle 302 rotates in the first direction from the starting position, grasps the fastener end 602 while the anchor end 603 is moved into position over the aperture in the suture housing 301, and continues to rotate into tissue in a curved path on a plane orthogonal to tissue, inserting the fastener end 602 into the anchor end 603. At the end position (see FIGS. 3A and 3C), the suturing needle 302 automatically rotates in the second direction to return to the starting position. As the suturing needle 302 returns to the starting position, the arm 307 of the suturing needle 302 comes into contact with the anchor end 603. The anchor end 603 is pushed out of the aperture in the suture housing 301 by the arm 307 of the suturing needle 302, allowing a next suture to have its fastener end 602 to move into position for grasping by the suturing needle 302. The fastener end 602 is released from the suture magazine 600 as the suture needle 302 and grasping edge 309 grasp the fastener end 602 and drag the fastener end 602 along a curved path to be inserted through the anchor end 603. The elastic members 601 apply a pulling force to the suture movers 606 which in turn apply a pushing force to the fastener end 602 and the anchor end 603, allowing another fastener end 602 and anchor end 603 to move into position to be grappled by the needle 302. When the fastener end 602 is inserted into the anchor end 603, the fastener end 602 is configured to be pulled through or locked within the anchor end 603 upon insertion to retain the suture under tension.

In an implementation incorporating a spring, after the fastener end 602 is released from the notch of the belt as the suturing needle 302 grasps the fastener end 602 and drags the fastener end 602 along a curved path to be inserted into the anchor end 603, the spring applies a pushing force to the anchor end 603 that urges the belt and the anchor end 603 forward, allowing another fastener end 602 to move into position to be grappled by the needle 302. When the fastener end 602 is inserted into the anchor end 603, the fastener end 602 is configured to lock with the anchor end 603 upon insertion to retain the suture under tension.

In an alternate embodiment, a suture magazine can include a belt having one or more notches, and at least one suture. The belt is positioned parallel to the anchor end 603. The belt may be made of rubber or another elastic material. The fastener end 602 is releasably secured to the notch of the belt. In one implementation, a crossbar can be attached to the belt. The crossbar has a first end and a second end. The first end is fixed to the belt, and the second end is in contact with the anchor end 603. A spring may be located behind the crossbar and positioned behind the anchor end 603.

Figure 7A:
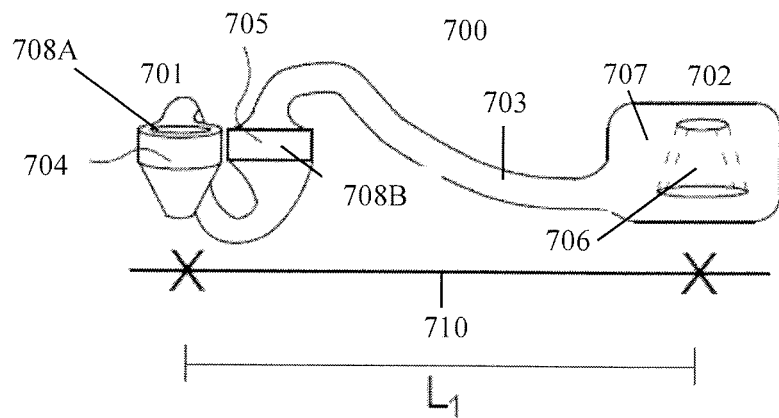
FIGS. 7A-7D shows an automatic suture tightening technique in accordance with an implementation of the invention.
Figure 7B:
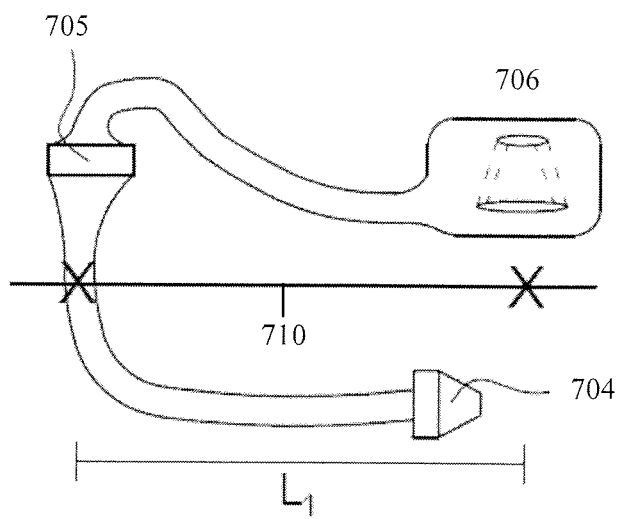
Figure 7C:
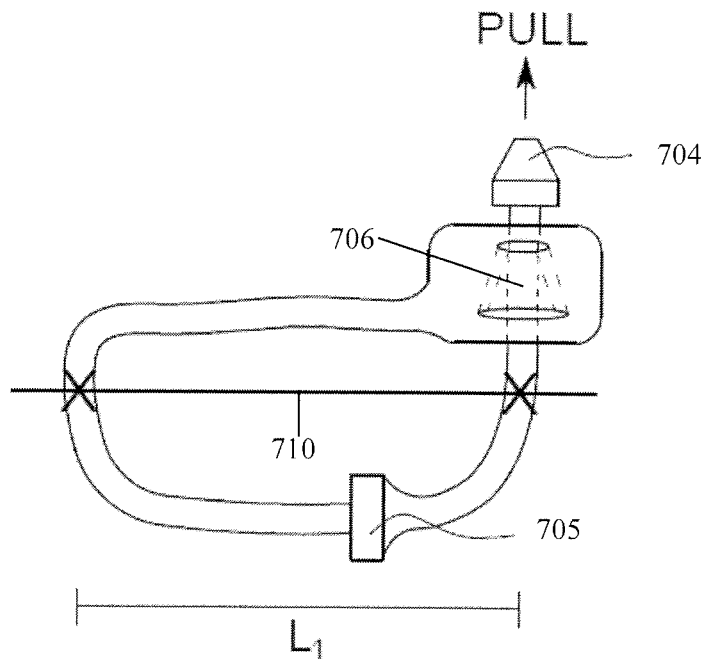
Figure 7D:
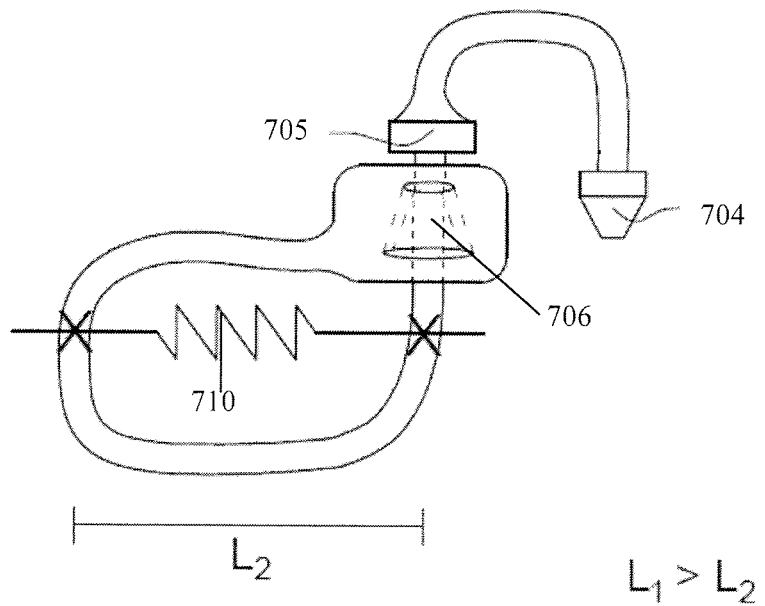

FIGS. 7A-7D show an automatic suture tightening technique. In FIG. 7A, a suture 700 is shown in a starting position over top of tissue 710. Next, as shown in FIG. 7B, the first fastener mechanism 704 of the fastener end 701 is inserted through an entry point of the tissue 710 and carried through the tissue 710 along a curved path by a suturing needle. In this embodiment, the suturing needle pushes the first fastener mechanism 704 along the fastener grasping edge 708A. As the suturing needle continues along the curved path and reaches an ending position, as shown in FIG. 7C, the first fastener mechanism 704 is pushed through the chamber 706 of the anchor end 702. The suture thread 703 pulls the second fastener mechanism 705 through the tissue 710 along the same curved path as first fastener mechanism 704. As the suture 700 is released from the suturing device, the fastener grasping edge 708A can rest on top of the anchor housing 707. At this stage, there is no tension on the suture thread 703. As shown in FIG. 7D, after the first fastener mechanism 704 is pulled in an upward direction, the second fastener mechanism 705 is pulled through the chamber 706 of the anchor end 702 and causes the tissue 710 to be pulled together. The suture 700 is designed so that when the second fastener mechanism 704 is pulled through the chamber 706 of the anchor end 702, a predetermined tension is created throughout the suture thread 703. At this point, the fastener grasping edge 708B prevents the second fastener mechanism 705 from moving backward through the chamber 706 of the anchor end 702.

Figure 8:
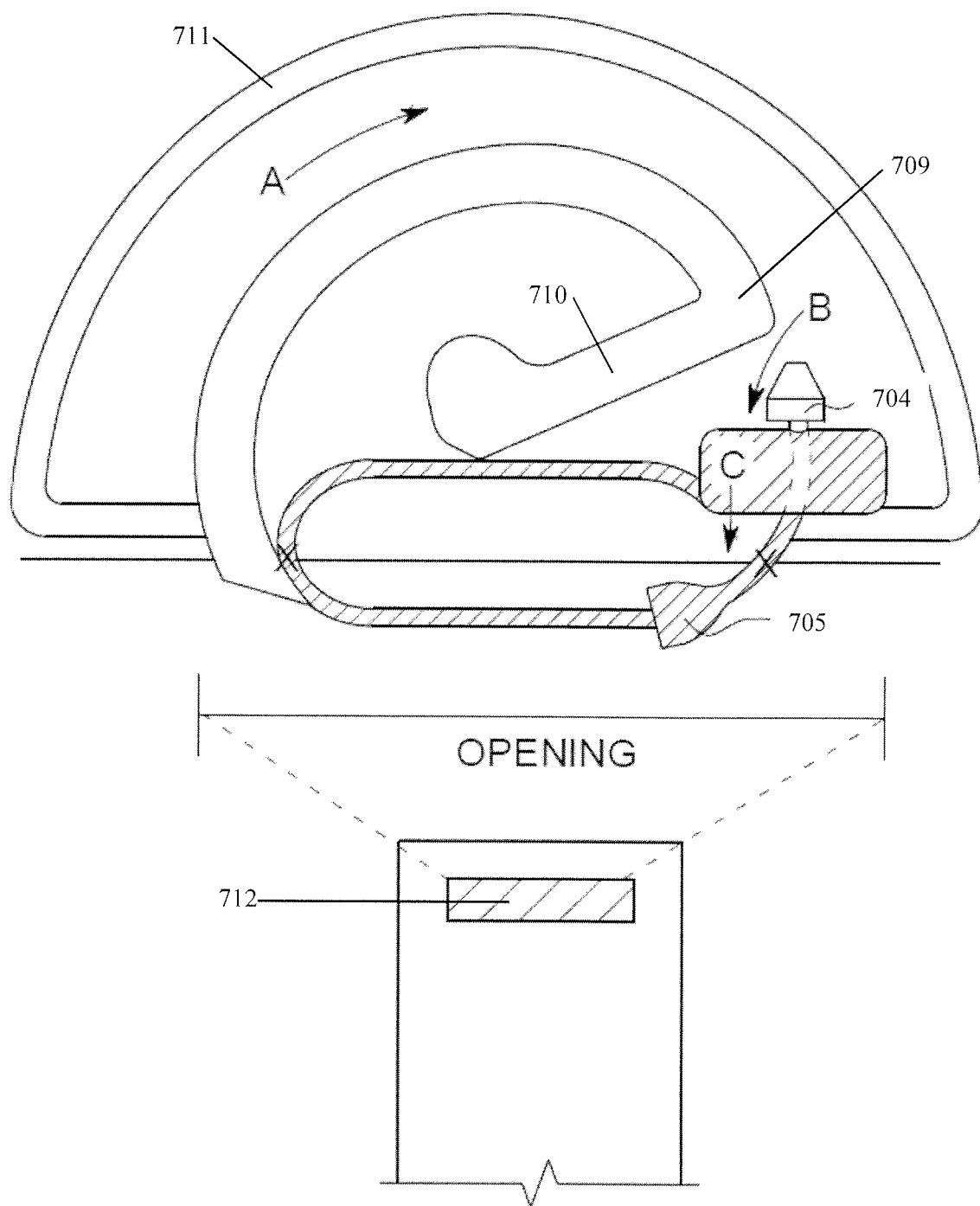
FIG. 8 shows a manual suture tightening technique in accordance with an implementation of the invention.
Figure 9A:
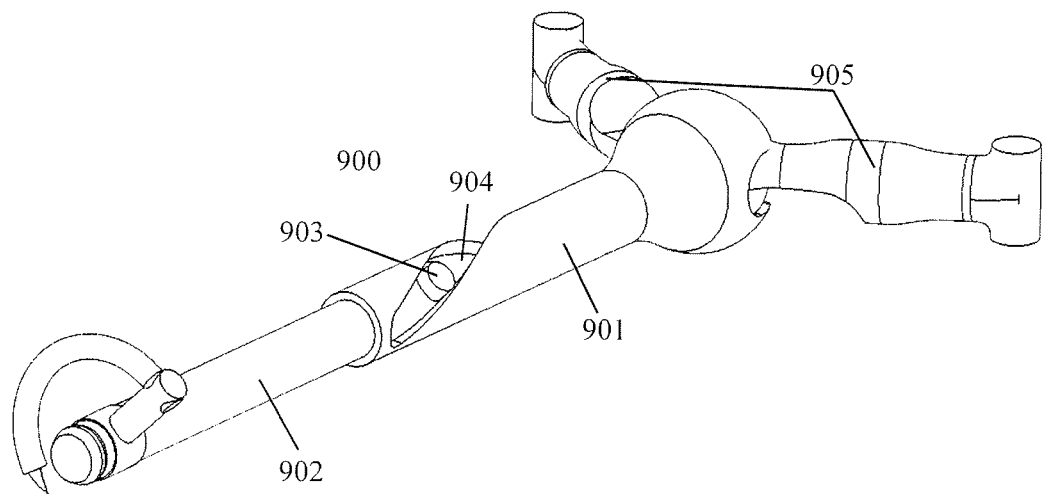
FIG. 9A shows a side view of a drive system in accordance with an implementation of the invention.
Figure 9B:
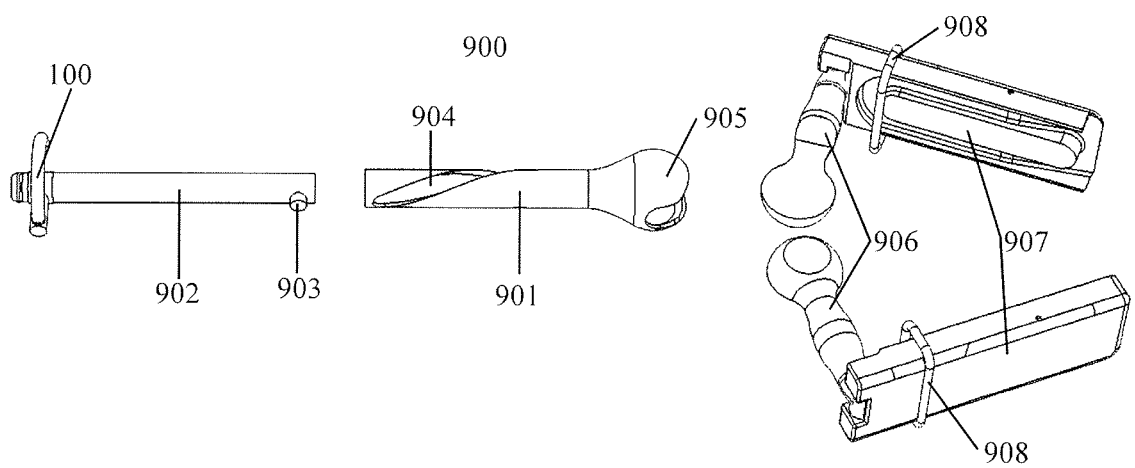
FIG. 9B shows a side view of an exploded view of a drive system in accordance with an implementation of the invention.
Figure 9C:
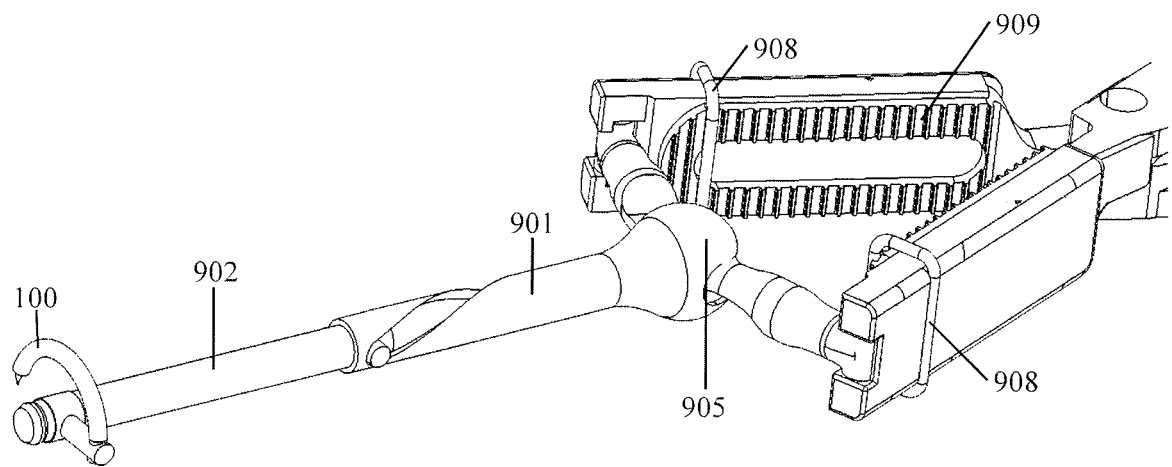
FIGS. 9C-9D show a view of a drive system attached to handles in the open and closed positions in accordance with an implementation of the invention.
Figure 9D:
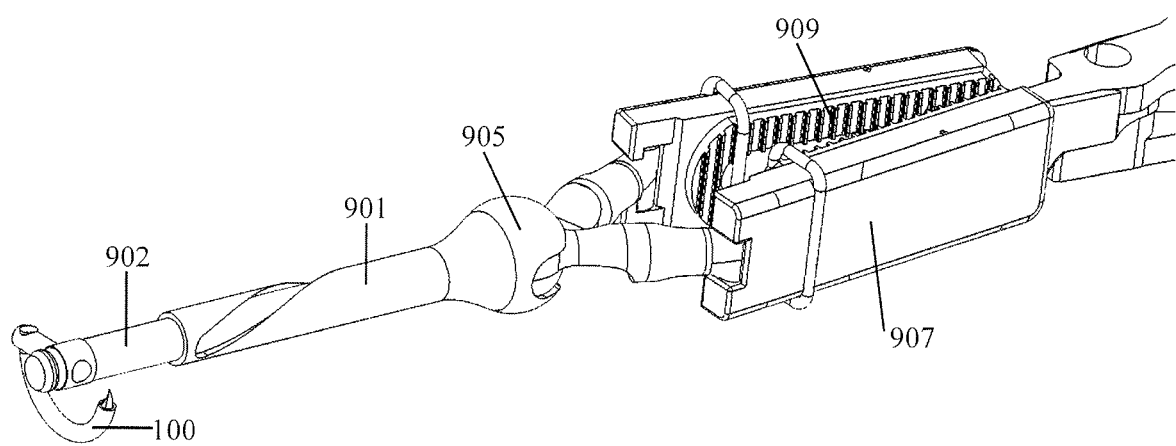
Figure 9E:
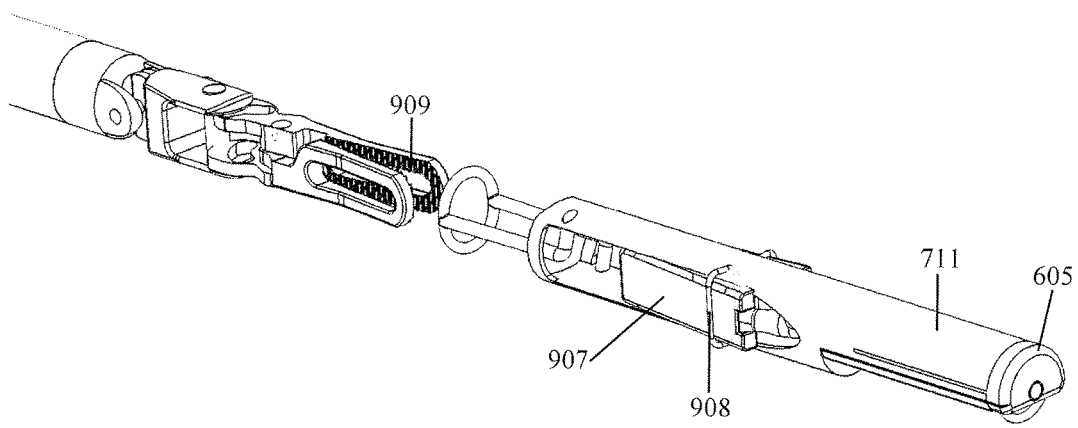
FIG. 9E shows the grasping clamp and the suturing device apart and in the end position.
Figure 9F:
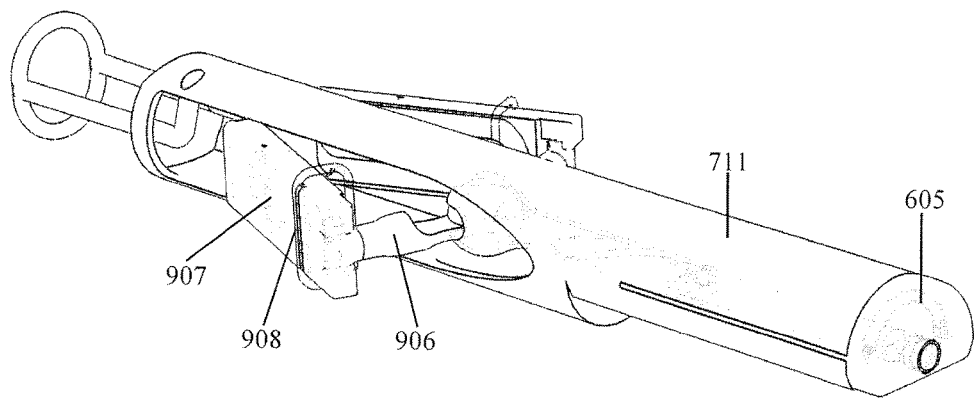
FIG. 9F shows the suturing device in the start position.

In another implementation, as shown in FIG. 8, in accordance with an implementation of a suture as described with respect to FIG. 4, the surgeon may manually grasp the first fastener mechanism 704 with a separate laparoscopic instrument and pull the first fastener mechanism 704 upward to tighten the suture thread 703 until the second fastener mechanism 705 is pulled through the chamber 706 to provide the desired tension on the suture. In another implementation, the surgeon may manually grasp the suture guide loop with a separate laparoscopic instrument and pull the suture guide loop upward to tighten the suture thread 703. Alternatively, the suturing device may have a hook positioned on the exterior of the suture housing, and the surgeon may manually tighten the suture using the hook rather than using an additional laparoscopic instrument.

As shown in FIG. 8, as the base 709 and the arm 710 return to the starting position, the base 709 pushes the anchor end 702 through the suture housing aperture 711, allowing the next fastener end 701 to be moved into position by the elastic member 601 and the suture mover 606 (not shown in this figure).

In another implementation, the suture housing of the suturing device 300 may have a clamp positioned along the interior surface of the suture housing that grasps the suture guide loop as the fastener end 702 enters the anchor end 703. As the suturing device is pulled away from tissue, the suture is tightened, and the clamp releases the suture guide loop once the suture reaches a predetermined tension. In an alternate embodiment, the clamp can grasp the suture guide loop as the fastener end 702 enters the anchor end 703.

In another implementation, the suture housing may have a catch attached to the interior surface of the suture housing to a side of the aperture, as described with respect to FIG. 5B. The catch can releasably grasp the suture guide loop of the fastener end 702 as the arm 710 of the suturing needle pushes down on the anchor end 703 when returning to the starting position. The catch automatically releasing the suture guide loop once the suture reaches a predetermined tension. Alternatively, the catch can releasably grasp the suture guide loop as the suturing device is pulled away from tissue and the catch automatically releasing the suture guide loop once the suture reaches a predetermined tension. In an alternate embodiment, the catch can be adapted to perform the same functions with a fastener mechanism that is described above with respect to a suture guide loop.

FIGS. 9A-9F show a drive system 900 that can be used to operate the suturing device 300 (see FIGS. 3A-3C). The drive system 900 includes a tube 901 and a rod 902. The diameter of the rod 902 is smaller than the diameter of the tube 901. The rod 902 may include one or more protrusions 903 positioned on the exterior surface of the rod 902 towards the proximal end. The tube 901 may have one or more grooves 904 that extend in a spiral manner from a proximal end of the tube 901 towards the distal end of the tube 901. Each groove 904 can correspond to one of the one or more protrusions 903. The one or more protrusions 903 attached to the rod 902 are configured to move along the one or more grooves 904 within the tube 901.

In one implementation, the proximal end of the rod 902 may abut a hub 905, and the distal end of the rod 902 is coupled to a shaft 311 of a suturing needle. The shaft can in the tube 901 and the rod 902. The tube 901 can have the hub 905 positioned at the proximal end of the tube 901. The rod 902 is configured to remain fixed along a direction of a rod axis of the shaft while being able to rotate about the rod axis. The tube 901 is configured to remain fixed in a radial direction while being movable forward and backward along the rod axis.

In a starting position, the rod 902 is positioned inside the tube 901, where the protrusions 903 lay on the grooves 904 of the tube 901, and the hub 905 of the tube 901 meets the proximal end of the rod 902. As a force pushes on the hub 905, the grooves 904 engage the protrusions 903 of the rod 902 and the tube 901 drives along the rod 902 from the proximal end of the rod 902 to the distal end of the rod 902, thereby rotating the rod 902 forward as the protrusions 903 travel along the grooves 904 of the tube 901. Once the force is withdrawn from the proximal end of the tube 901, the tube 901 reverses direction from the distal end of the rod 902 to the proximal end of the rod 902, thereby rotating the rod 902 backward as the protrusions 903 travel along the grooves 904 in the opposite direction.

In order to connect the drive system 900 to a surgical device, such as a laparoscopic device, the distal end of the hub handles 906 are attached to the hub 905. At the proximal end of the hub handles 906, clamp head receiving members 907 are attached to receive a grasping clamp 909 from a surgical device. Clips 908 are positioned around the clamp head receiving members 907 and the grasping clamp 909 so that the clamp head receiving members 907 and the grasping clamp 909 are secured to one another.

In one implementation, the rod 902 of the suturing needle 302, as described with respect to FIG. 6B, is connected to the distal end of the rod 902. Therefore, when the tube 901 drives along the rod 902, both the rod 902 and the suturing needle 302 rotate in a first direction, which allows the suturing needle 302 to deploy from the suture housing 301 and grasp the fastener end 602. As the suturing needle 302 rotates and inserts the fastener end 602 into the anchor end 603, the protrusions 903 have traveled the complete length of the grooves 904 of the tube 901, and the rod 901 ceases rotational movement. When the force is withdrawn from the proximal end of the tube 901, the fastener end 602 remains locked in the anchor end 603, and the tube 901 reverses direction causing both the rod 902 and the suturing needle 302 to rotate in a second direction until the protrusions 903 travel the length of the grooves 904 in the opposite direction, retracting the suturing needle 302 into the suture housing 301. As the suturing needle 302 retracts back in to the suture housing 301, the arm 710 of the suturing needle 302 will push down on the anchor end 603, allowing the entire suture to release from the device.

In one implementation, the hub 905 of the tube 901 can be coupled to a manual trigger. A trigger, as described with respect to FIG. 4, may apply a force to the hub 905 of the tube 901, engaging the drive system 900. The trigger is connected to the proximal end of a manual arm. The manual arm can be the laparoscope. The drive system 900 can be connected to the distal end of the stem of the laparoscope. Upon the surgeon squeezing the trigger, the tube 901 is propelled forward along the rod 902, resulting in both the rod 902 and the suturing needle 302 rotating in a first direction. Once the trigger is released, the tube 901 reverses direction, causing both the rod 902 and the suturing needle 302 to rotate in a second direction until the protrusions 903 travel the length of the grooves 904 in the opposite direction, retracting the suturing needle 302 into the suture housing 301.

In another implementation, the hub 905 of the tube 901 can be coupled to a robotic arm or incorporated as a robotic arm as part of a robotic-assisted surgical system. A robotic-assisted surgical system forceps arm, may apply a force to the hub 905 of the tube 901, engaging the drive system 900. The robotic-assisted surgical forceps arm is attached to a main hub of the robotic-assisted surgical system at its proximal end, and includes forceps at its distal end. The main hub of the robotic-assisted surgical system contains one or more robotic arms that the surgeon can control from a distance at a console. A sheath made of a non-ridged sterile material may be used to connect the proximal end of the suture housing 301 of the suturing device 300, to the distal end of the robotic arm.

Forceps may be positioned at the proximal end of the drive system 900. A hinge may be inserted into the forceps of the robotic-assisted surgical forceps arm. The hinge may include a spring tensioned to keep the forceps open at a certain angle when the hinge is inserted into the forceps. Upon closing the forceps, the hinge compresses and lengthens the forceps. The lengthened forceps come into contact with the tube 901 and apply a force to the tube 901 that propels the tube 901 forward along the rod 902, which causes the rod 902 and the suturing needle 302 to rotate in the first direction. When the surgeon opens the forceps, the tube 901 reverses direction causing both the rod 902 and the suturing needle 302 to rotate in a second direction until the protrusions 903 travel the length of the grooves 904 in the opposite direction, retracting the suturing needle 302 into the suture housing 301.

Figure 10:
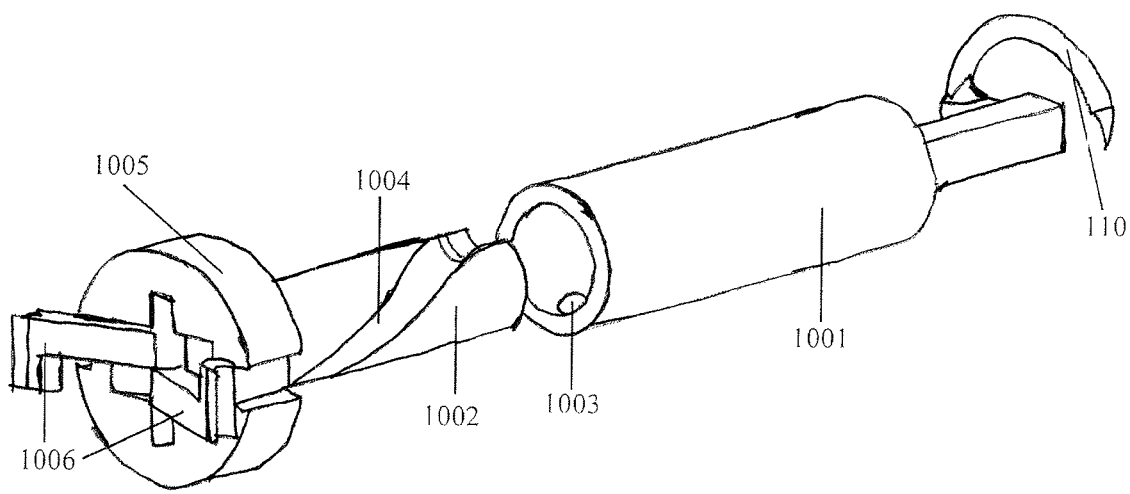
FIG. 10 shows a side view of an alternative drive system in accordance with an implementation of the invention.

FIG. 10 shows a side view of an alternative drive system in accordance with an implementation of the invention. Referring to FIG. 10, drive system 1000 can be used to operate a suturing device. The drive system 1000 includes a tube 1001 and a rod 1002. The diameter of the rod 1002 is smaller than the diameter of the tube 1001. The tube 1001 may include one or more protrusions 1003 positioned on the interior surface of the tube 1001 towards the proximal end. The rod 1002 may have one or more grooves 1004 that extend in a spiral manner from a proximal end of the rod 1002 towards the distal end of the rod 1002. Each groove 1004 can correspond to one of the one or more protrusions 1003. The one or more protrusions 1003 attached to the tube 1001 are configured to move along the one or more grooves 1004 within the rod 1002.

In one implementation, the proximal end of the tube 1001 may abut a hub 1005, and the distal end of the tube 1001 is coupled to a rod 1002 of a suturing needle. The rod 1002 can have the hub 1005 positioned at the proximal end of the rod 1002. The hub 1005 is attached to the hub handles 1006 which are configured to attach to a forceps or laparoscopic device. The tube 1001 is configured to remain fixed along a direction of a rod axis of the rod 1002 while being able to rotate about the rod axis. The rod 1002 is configured to remain fixed in a radial direction while being movable forward and backward along the rod axis.

In a starting position, the rod 1002 is positioned inside the tube 1001, where the protrusions 1003 lay on the grooves 1004 of the rod 1002 and the hub 1005 of the rod 1002 meets the proximal end of the tube 1001. As a force pushes on the hub 1005, the grooves 1004 engage the protrusions 1003 of the tube 1001 and the rod 1002 drives along the tube 1001 from the proximal end of the tube 1001 to the distal end of the tube 1001, thereby rotating the tube 1001 forward as the protrusions 1003 travel along the grooves 1004 of the rod 1002. Once the force is withdrawn from the proximal end of the rod 1002, the rod 1002 reverses direction from the distal end of the tube 1001 to the proximal end of the tube 1001, thereby rotating the tube 1001 backward as the protrusions 1003 travel along the grooves 1004 in the opposite direction.

Suturing devices, needles, sutures, and drive systems are presented herein.

According to some embodiments, a suture is provided comprising: a fastener end; an anchor end; and a suture thread connected to and extending between the fastener end and the anchor end. The fastener end can comprise a first and second conical shaped structure, the first and second conical shaped structure having a top and a bottom, the suture thread fixed to the top, the bottom being larger than the top. The anchor end can comprise an anchor housing and a chamber, the interior surface of the chamber having a conical shape. The first conical shaped structure can be configured to slide through the anchor housing and remain locked in the anchor end once the first conical shaped structure is inserted through the chamber of the anchor end. The second conical shaped structure can be configured to be pulled through the chamber, wherein the pulling of the second conical shaped structure through the chamber tensions a suture to a predetermined tension level.

According to some embodiments, a suture magazine is provided comprising: a belt having one or more notches; at least one suture having a fastener end, an anchor end, and a suture thread connected to and extending between the fastener end and the anchor end, the anchor end positioned parallel to the fastener end, the fastener end releasably secured to the belt; a crossbar having a first end and a second end, the first end fixed to the belt, the second end in contact with the anchor end; and a spring in tension with the second end of the crossbar, wherein the spring applies a pushing force to the anchor end, urging the belt forward once a fastener has been released. The fastener end can comprise a curved enclosure having a ridged surface, a top, and a bottom, the suture thread fixed to the top, the bottom having a suture guide loop positioned laterally. The anchor end can comprise a rectangular enclosure and a chamber, the interior surface of the chamber having at least one shoulder.

Any reference in this specification to "one implementation," "an implementation," "example implementation," etc., means that a particular feature, structure, or characteristic described in connection with the implementation is included in at least one implementation of the invention. The appearances of such phrases in various places in the specification are not necessarily all referring to the same implementation. In addition, any elements or limitations of any invention or implementation thereof disclosed herein can be combined with any and/or all other elements or limitations (individually or in any combination) or any other invention or implementation thereof discloses herein, and all such combinations are contemplated with the scope of the invention without limitation thereto.

It should be understood that the examples and implementations described herein are for illustrative purposes only and that various modifications or changes in light thereof will be suggested to persons skilled in the art and are to be included within the spirit and purview of this application.

What is claimed is:

1. A suture magazine comprising:
    a set of sutures, each suture of the set of sutures comprising a fastener, an anchor, and a suture thread extending between the fastener and the anchor;
    a suture mover supporting the set of sutures between a first end and a second end of the suture magazine; and
    a biasing element coupled to the suture mover and biasing the set of sutures toward the first end of the suture magazine, the biasing element contributing to an advancing mode of the suture magazine wherein, in the advancing mode, a leading suture of the set of sutures is displaced from the first end of the suture magazine by a compressive force applied by at least one of the biasing element and the suture mover, wherein the leading suture of the set of sutures is exposed at the first end and aligned with a suture needle,
    wherein the suture magazine comprises:
        a first operation mode in which a piercing end of the suture needle is rotated in a first direction and engages the fastener of the leading suture to displace the fastener through a tissue and through the anchor, and
        a second operation mode in which the suture needle is rotated in a second direction opposite the first direction and engages the anchor of the leading suture to displace the anchor from the first end of the suture magazine.

2. The suture magazine of claim 1, wherein the fastener of each suture of the set of sutures comprises a locking body with a grasping edge, the anchor of each suture of the set of sutures comprises an anchor housing with a chamber terminating at a locking surface, and wherein, for a respective suture of the set of sutures, the grasping edge of the locking body of the respective suture is configured to pass through the chamber of the anchor of the respective suture and be retained at the locking surface of the anchor end of the respective suture.

3. The suture magazine of claim 2, wherein the fastener of each suture of the set of sutures comprises a cavity configured to allow compression of the fastener as it passes through the chamber of the anchor of the respective suture, and wherein the grasping edge of the fastener extends laterally from the suture thread of the respective suture.

4. The suture magazine of claim 2, wherein the respective suture further comprises a tensioning body positioned at a location along the suture thread between the fastener and the anchor of the respective suture, wherein, in a sutured mode, the location defines a predetermined tension when at least one of the tensioning body and the fastener passes through tissue and through the anchor of the respective suture.

5. The suture magazine of claim 1, wherein the suture mover defines a set of parallel tracks supporting the set of sutures in a serial arrangement.

6. The suture magazine of claim 5, wherein the biasing element is positioned toward the second end of the suture magazine, behind the suture mover.

7. The suture magazine of claim 5, wherein the biasing element comprises at least one of a spring and an elastic member behind the suture mover.

8. The suture magazine of claim 1, wherein in coordination with the second operation mode, the biasing element advances at least a portion of the suture mover toward the first end, thereby advancing remaining sutures of the set of sutures toward the first end.

9. The suture magazine of claim 8, wherein the biasing element comprises a spring coupled to the portion of the suture mover configured to advance remaining sutures of the set of sutures toward the first end.

10. The suture magazine of claim 1, wherein the suture mover comprises at least one notch that secures the fasteners of remaining sutures of the set of sutures in position.

11. The suture magazine of claim 1, wherein the suture magazine is configured to be released from a medical device housing and disposed.

* * * * *